(12) United States Patent
Jang et al.

(10) Patent No.: US 10,046,061 B2
(45) Date of Patent: Aug. 14, 2018

(54) SITE-SPECIFIC INSULIN CONJUGATE

(71) Applicant: HANMI PHARM. CO., LTD., Hwaseong-si, Gyeonggi-do (KR)

(72) Inventors: Myung Hyun Jang, Seoul (KR); Dae Jin Kim, Hwaseong-si (KR); Sang Youn Hwang, Hwaseong-si (KR); Hyun Uk Kim, Busan (KR); Sung Youb Jung, Suwon-si (KR); Se Chang Kwon, Seoul (KR)

(73) Assignee: HANMI PHARM. CO., LTD, Hwaseong-si (KR)

( * ) Notice: Subject to any disclaimer, the term of this patent is extended or adjusted under 35 U.S.C. 154(b) by 0 days.

(21) Appl. No.: 14/770,214

(22) PCT Filed: Feb. 26, 2014

(86) PCT No.: PCT/KR2014/001597
§ 371 (c)(1),
(2) Date: Aug. 25, 2015

(87) PCT Pub. No.: WO2014/133327
PCT Pub. Date: Sep. 4, 2014

(65) Prior Publication Data
US 2016/0000931 A1    Jan. 7, 2016

(30) Foreign Application Priority Data
Feb. 26, 2013  (KR) .................. 10-2013-0020703

(51) Int. Cl.
| | |
|---|---|
| *C07K 16/46* | (2006.01) |
| *A61K 38/28* | (2006.01) |
| *A61K 47/48* | (2006.01) |
| *C07K 14/62* | (2006.01) |
| *C07K 17/08* | (2006.01) |
| *A61K 47/68* | (2017.01) |

(52) U.S. Cl.
CPC ........ *A61K 47/48369* (2013.01); *A61K 38/28* (2013.01); *A61K 47/68* (2017.08); *A61K 47/6811* (2017.08); *A61K 47/6889* (2017.08); *C07K 14/62* (2013.01); *C07K 17/08* (2013.01); *C07K 2319/30* (2013.01)

(58) Field of Classification Search
CPC . A61K 38/28; A61K 47/48215; A61K 47/369
See application file for complete search history.

(56) References Cited

U.S. PATENT DOCUMENTS

| | | | |
|---|---|---|---|
| 2009/0285780 A1 | 11/2009 | Lee | |
| 2012/0003712 A1* | 1/2012 | Song | ................ A61K 47/48215 435/183 |
| 2013/0028918 A1 | 1/2013 | Song et al. | |

FOREIGN PATENT DOCUMENTS

| | | |
|---|---|---|
| CN | 102869371 A | 1/2013 |
| KR | 10-2011-0111267 A | 10/2011 |
| KR | 10-2011-0134210 A | 12/2011 |
| WO | 2010107256 A2 | 9/2010 |
| WO | 2011/122921 A2 | 10/2011 |
| WO | 2011/159895 A2 | 12/2011 |
| WO | 2012/122860 A1 | 9/2012 |
| WO | 2012165915 A2 | 12/2012 |

OTHER PUBLICATIONS

Saudi Arabian Patent Office; Communication dated Apr. 23, 2016 in counterpart application No. 515360887.
Kenneth D. Hinds et al., "Effects of PEG conjugation on insulin properties," Advanced Drug Delivery Reviews, 2002, pp. 505-530, vol. 54, No. 4.
Jens Brange et al., "Insulin analogs with improved pharmacokinetic profiles," Advanced Drug Delivery Reviews, 1999, pp. 307-335, vol. 35, No. 2-3.
Peter Kurtzhals et al., "Correlations of Receptor Binding and Metabolic and Mitogenic Potencies of Insulin Analogs Designed for Clinical Use," Diabetes, Jun. 2000, pp. 999-1005, vol. 49, No. 6.
International Searching Authority, International Search Report of PCT/KR2014/001597 dated May 22, 2014.
Colombian Patent Office, Communication dated Dec. 21, 2016, issued in corresponding Colombian Application No. 15175553.
European Patent Office, Communication dated Sep. 16, 2016, issued in corresponding European Application No. 14757574.0.
Japanese Patent Office communication dated Nov. 14, 2017 in counterpart application No. 2015-559200.
Russian Patent and Trademark Office; Communication dated Jan. 31, 2018 in counterpart application No. 2015133462/10.
Patel et al., "Conjugation with Cationic Cell-Penetrating Peptide Increases Pulmonary Absorption of Insulin," Mol. Pharm. 2009; vol. 6, No. 2; pp. 492-503.
State Intellectual Property Office of the P.R.C.; Communication dated Feb. 2, 2018 in counterpart application No. 201480009429.5.

* cited by examiner

*Primary Examiner* — Gyan Chandra
(74) *Attorney, Agent, or Firm* — Sughrue Mion, PLLC (57) ABSTRACT

Provided are an insulin conjugate having improved insulin receptor binding affinity and increased activity, in which a non-peptidyl polymer and an immunoglobulin Fc region are site-specifically linked to an amino acid residue of the insulin beta chain excluding the N-terminus thereof via a covalent bond, a long-acting formulation including the same, and a preparation method thereof. The insulin conjugate of the present invention is used to provide an insulin formulation which exhibits a remarkably increased in vivo activity of the peptide.

30 Claims, 5 Drawing Sheets

SEQUENCE LISTING

```
<160> NUMBER OF SEQ ID NOS: 2

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
 1               5                  10                  15

Glu Asn Tyr Cys Asn
            20

<210> SEQ ID NO 2
<211> LENGTH: 30
<212> TYPE: PRT
<213> ORGANISM: Homo sapiens
```

```
<400> SEQUENCE: 2

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Thr
             20                  25                  30
```

SITE-SPECIFIC INSULIN CONJUGATE

CROSS REFERENCE TO RELATED APPLICATIONS

This is a National Stage of International Application No. PCT/KR2014/001597 filed Feb. 26, 2014, claiming priority based on Korean Patent Application No. 10-2013-0020703 filed Feb. 26, 2013, the contents of all of which are incorporated herein by reference in their entirety.

BACKGROUND OF THE INVENTION

1. Field of the Invention

The present invention relates to a conjugate in which a non-peptidyl polymer linker and an immunoglobulin constant region are specifically linked to an amino acid residue of the insulin beta chain excluding the N-terminus thereof via a covalent bond, and a preparation method thereof.

2. Description of the Related Art insulin is a peptide secreted from the beta cells of the human pancreas as a material which plays a very important role in controlling the blood glucose level in the body. In cases where insulin is not properly secreted or insulin as secreted does not properly act in the body, blood glucose in the body cannot be controlled and is increased, thereby inducing the state referred to as diabetes. The case as stated above is referred to as type 2 diabetes mellitus, and the case where insulin is not secreted from the pancreas to increase blood glucose is referred to as type 1 diabetes mellitus. Type 2 diabetes mellitus is treated with an oral hypoglycemic agent including a chemical material as the main component, and in certain patients, is also treated with insulin. On the other hand, treatment of type 1 diabetes mellitus necessarily requires the administration of insulin.

The insulin therapy as widely used at the present time is a method of administering insulin via injection before and after meals. However, such insulin therapy requires that it be constantly administered three times daily, and therefore causes much suffering and inconvenience in patients. In order to overcome such problems, various attempts have been made. One of them was an attempt to deliver peptide drugs into the body by way of inhalation through oral or nasal cavities by increasing the biological membrane permeability of peptide drugs. However, such a method shows a significantly low efficiency of peptide delivery in the body compared to injection. Accordingly, there are still many difficulties in maintaining the in vivo activity of peptide drugs in the required conditions.

Further, a method for delaying absorption after subcutaneous administration of excessive drugs has been attempted. According to this, a method for maintaining blood drug concentration through only a single administration daily has been presented. Some have been approved as medicinal products (e.g. Lantus, Sanofi-aventis) and are currently administered to patients. The study to modify insulin with fatty acids to strengthen the binding of an insulin polymer and to extend the duration through binding to albumin present at the site of administration and in blood has progressed, and drugs produced using such a method have been approved as medicinal products (Levemir, NovoNordisk). However, such methods have the side effect of causing pain at the site of administration, and additionally, the administration interval of a single injection daily still causes significant inconvenience for patients.

Meanwhile, it was reported that the N- or C-terminal region, i.e. the amino acid residue at the position 29 of the insulin beta chain, does not significantly influence binding of insulin to the insulin receptor (Jens Brange and Aage Volund, Adv. Drug Deliv. Rev., 35(2-3): 307-335 (1999); Peter Kurtzhals et al., Diabetes, 49(6): 999-1005 (2000)).

Accordingly, the present inventors have studied to develop a method of modifying an amino acid residue at the C-terminal region of the insulin beta chain with a non-peptidyl polymer and an immunoglobulin constant region, and they found that this method is used to prepare a conjugate having higher binding affinity to the insulin receptor than conjugates prepared by modifying other sites of insulin such as a N-terminus, thereby completing the present invention.

SUMMARY OF THE INVENTION

An object of the present invention is to provide an insulin conjugate which is prepared by site-selectively linking an immunoglobulin Fc region to an amino acid residue of the insulin beta chain excluding the N-terminus thereof via a non-peptidyl polymer, and a preparation method thereof.

BRIEF DESCRIPTION OF THE DRAWINGS

FIGS. 1A to 1E show a profile and an SDS-PAGE gel photograph of mono-pegylated insulin purified using a Source 15S column;

FIGS. 2 to 3 show insulin-PEG resulting from site-specific pegylation at the $29^{th}$ amino acid residue of the beta chain;

DETAILED DESCRIPTION OF THE PREFERRED EMBODIMENTS

In an aspect to achieve the above object, the present invention provides an insulin conjugate, characterized in that insulin and an immunoglobulin Fc region are linked to each other via a non-peptidyl polymer linker selected from the group consisting of polyethylene glycol, polypropylene glycol, an ethylene glycol-propylene glycol copolymer, polyoxyethylated polyol, polyvinyl alcohol, polysaccharide, dextran, polyvinyl ethyl ether, a biodegradable polymer, a lipid polymer, chitin, hyaluronic acid, and a combination thereof, and one end of the non-peptidyl polymer is linked to an amino acid residue of the insulin beta chain excluding the N-terminus thereof and the other end thereof is linked to the immunoglobulin Fc region.

Preferably, the non-peptidyl polymer may be linked to any one of the amino acid residues at positions 20 to 29 of the insulin beta chain.

More preferably, the non-peptidyl polymer may be linked to any one of the amino acid residues at positions 25 to 29 of the insulin beta chain.

Much more preferably, the non-peptidyl polymer may be linked to the lysine residue at position 29 of the insulin beta chain.

Preferably, the amino acid residue of the insulin beta chain, to which the non-peptidyl polymer is linked, may have an amine group or a thiol group.

Preferably, the insulin may be a native insulin, or a variant which is prepared by any one method of substitution, addition, deletion, and modification of some amino acids of native insulin or by a combination thereof, an insulin derivative, an insulin agonist, or a fragment thereof.

Preferably, both ends of the non-peptidyl polymer may be linked to an amine group or a thiol group of the side chain of the amino acid residue of an immunoglobulin Fc region and the insulin beta chain, respectively.

Preferably, the amino acid may be a naturally occurring or non-naturally occurring amino acid.

Preferably, the immunoglobulin Fc region may be aglycosylated.

Preferably, the immunoglobulin Fc region is composed of one to four domains selected from the group consisting of CH1, CH2, CH3 and CH4 domains.

Preferably, the immunoglobulin Fc region may further include a hinge region.

Preferably, the immunoglobulin Fc region may be an Fc region derived from IgG, IgA, IgD, IgE or IgM.

Preferably, each domain of the immunoglobulin Fc region may be a hybrid of domains of a different origin derived from an immunoglobulin selected from the group consisting of IgG, IgA, IgD, IgE, and IgM.

Preferably, the immunoglobulin Fc region may be a dimer or a multimer composed of single-chain immunoglobulins composed of domains of the same origin.

Preferably, the immunoglobulin Fc region may be an IgG4 Fc region.

Preferably, the immunoglobulin Fc region may be a human aglycosylated IgG4 Fc region.

Preferably, the non-peptidyl polymer may bind to the amine group or thiol group of the side chain of the amino acid residue of the insulin beta chain to form a peptide, hemithioacetal, imine or thiodioxopyrrolidinyl bond.

Preferably, both ends of the non-peptidyl polymer may each independently have a reactive group selected from the group consisting of an aldehyde group, a propionaldehyde group, a butyraldehyde group, a maleimide group, and a succinimide derivative.

Preferably, the succinimide derivative may be succinimidyl carboxymethyl, succinimidyl valerate, succinimidyl methyl butanoate, succinimidyl methyl propionate, succinimidyl butanoate, succinimidyl propionate, N-hydroxysuccinimide, or succinimidyl carbonate.

Preferably, both ends of the non-peptidyl polymer may have a butyraldehyde reactive group or a succinimidyl valerate reactive group, respectively.

In another aspect, the present invention provides a long-acting insulin formulation having improved in vivo duration and stability, including the insulin conjugate.

Preferably, the formulation may be used for the treatment of diabetes.

In still another aspect, the present invention provides a preparation method of the insulin conjugate, including the steps of: (1) covalently linking a non-peptidyl polymer to an amino acid residue of the insulin beta chain excluding the N-terminus thereof; (2) isolating an insulin complex, in which the non-peptidyl polymer is covalently linked to the amino acid residue of the insulin beta chain excluding the N-terminus thereof, from the reaction mixture of (1); and (3) covalently linking an immunoglobulin Fc region to the other end of the non-peptidyl polymer of the isolated complex so as to produce an insulin conjugate, in which the immunoglobulin Fc region and insulin are linked to each end of the non-peptidyl polymer.

Preferably, the non-peptidyl polymer may bind to the amine group or thiol group of the side chain of the amino acid residue of the insulin beta chain to form a peptide, hemithioacetal, imine or thiodioxopyrrolidinyl bond.

Preferably, both ends of the non-peptidyl polymer may each independently have an aldehyde derivative, a maleimide derivative, or a succinimide derivative as a reactive group.

Preferably, both ends of the non-peptidyl polymer may be linked to an amine group or a thiol group of the amino acid residue of the insulin beta chain excluding the N-terminus thereof and an immunoglobulin Fc region, respectively.

Preferably, both ends of the non-peptidyl polymer may each independently have an aldehyde derivative or a succinimide derivative as a reactive group.

Preferably, Step (1) may be performed under an alkaline environment of pH 9.0±2.

Preferably, a molar ratio of the insulin and the non-peptidyl polymer in Step (1) may be 1:1.5 to 1:10.

Preferably, a molar ratio of the insulin complex and the immunoglobulin Fc region in Step (3) may be 1:1 to 1:10.

In an aspect to achieve the above object, the present invention provides an insulin conjugate, characterized in that insulin and an immunoglobulin Fc region are linked to each other via a non-peptidyl polymer linker selected from the group consisting of polyethylene glycol, polypropylene glycol, an ethylene glycol-propylene glycol copolymer, polyoxyethylated polyol, polyvinyl alcohol, polysaccharide, dextran, polyvinyl ethyl ether, a biodegradable polymer, a lipid polymer, chitin, hyaluronic acid, and a combination thereof, and one end of the non-peptidyl polymer is linked to an amino acid residue of the insulin beta chain excluding the N-terminus thereof and the other end thereof is linked to the immunoglobulin Fc region.

In the present invention, insulin is a kind of physiologically active peptide secreted from the pancreas when the blood glucose level becomes high, which functions to control blood glucose levels by causing the liver, skeletal muscles, and fat tissue to take up glucose from the blood and store it as glycogen, and by suppressing metabolism for using fat as an energy source. As used herein, the term 'insulin' includes insulin agonists, precursors, derivatives, fragments, or variants, as well as native insulin. Preferably, the insulin includes native insulin, fast-acting insulin, and long-acting insulin without limitation.

Native insulin is a hormone secreted from the pancreas and plays a critical role in the control of blood glucose levels by promoting the cellular uptake of glucose and inhibiting lipolysis. Insulin having a function of regulating blood glucose levels is produced from a proinsulin precursor without a function of regulating blood glucose levels, through a series of processes. The amino acid sequences of the native insulin are as follows.

```
-Alpha chain:
                                      (SEQ ID NO: 1)
Gly-Ile-Val-Glu-Gln-Cys-Cys-Thr-Ser-Ile-Cys-Ser- Leu-Tyr-Gln-Leu-Glu-Asn-Tyr-Cys-Asn -Beta chain:
                                      (SEQ ID NO: 2)
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Pro-Lys-Thr
```

Preferably, the insulin may be a native insulin, or a variant which is prepared by any one method of substitution, addition, deletion, and modification of some amino acids of native insulin or by a combination thereof, an insulin derivative, an insulin agonist, or a fragment thereof.

The insulin agonist denotes a substance that binds to the insulin receptor to show the biological activity equal to that of insulin, which is irrelevant to the structure of insulin.

The insulin derivative denotes a peptide which shows a sequence homology of at least 80% in an amino acid sequence as compared to the native insulin, has some groups of amino acid residues that are altered by chemical substitution (e.g. alpha-methylation, alpha-hydroxylation), removal (e.g. deamination) or modification (e.g. N-methylation, glycosylation, fatty acids), and has a function of controlling blood glucose in the body.

The insulin fragment denotes a fragment having one or more amino acids added or deleted at the amino or carboxyl terminus of insulin, in which the added amino acids may be non-naturally occurring amino acids (e.g. D-type amino acid), and this insulin fragment has a function of controlling the blood glucose level in the body.

The insulin variant denotes a peptide which differs from insulin in one or more amino acid sequences, and retains the function of controlling blood glucose in the body.

Further, the respective preparation methods of the insulin agonists, derivatives, fragments, and variants may be used individually or in combination. For example, the insulin peptide of the present invention also includes a peptide that has one or more amino acids different from those of native insulin and deamination of the N-terminal amino acid residue, and has a function of controlling the blood glucose level in the body.

In a specific embodiment, the insulin used in the present invention may be produced by a recombination technology, and it is also possible to synthesize the insulin by a solid phase method.

The insulin conjugate of the present invention is characterized in that it is prepared by covalently linking the insulin beta chain and an immunoglobulin Fc region to each end of the non-peptidyl polymer as a linker, in which the non-peptidyl polymer has reactive groups at both ends. Preferably, both ends of the non-peptidyl polymer may be linked to an amine group or a thiol group of the side chain of the amino acid residue of the immunoglobulin Fc region and the insulin beta chain, respectively.

In this regard, the amino acid may be a naturally occurring or non-naturally occurring amino acid, but there is no limitation, as long as the amino acid contains an amine group or a thiol group to form a covalent bond, together with the non-peptidyl polymer.

In the present invention, it was found that the insulin receptor binding affinity differs by varying the PEG-Fc-binding site on the insulin beta chain in the preparation of a conjugate of polyethylene glycol (PEG) and an immunoglobulin constant region (hereinafter, referred to as immunoglobulin Fc or Fc) to improve blood stability of insulin. Furthermore, the present inventors demonstrated a binding site that increases the binding affinity of insulin to improve its activity. For example, they identified a binding site that improves blood stability by binding with PEG-Fc and does not reduce activity without inhibiting binding with insulin receptors. In the case where the aloha chain of insulin is used to form a conjugate, its activity is remarkably reduced. Therefore, it was intended to explore an optimal binding site on the beta chain of insulin. As a result, it was confirmed that the binding site of the non-peptidyl polymer may be any amino acid residue having an amine group or a thiol group, excluding the N-terminus of the insulin beta chain.

Preferably, the non-peptidyl polymer may be linked to any one of the amino acid residues at positions 20 to 29 of the insulin beta chain. More preferably, the non-peptidyl polymer may be linked to any one of the amino acid residues at positions 25 to 29 of the insulin beta chain. Much more preferably, the non-peptidyl polymer may be linked to the lysine residue at position 29 of the insulin beta chain.

Preferably, the amino acid residue of the insulin beta chain, to which the non-peptidyl polymer is linked, may have an amine group or a thiol group. For example, the amino acid residue may be lysine, cysteine, or a derivative thereof, but is not limited thereto.

In a specific embodiment of the present invention, conjugates were prepared by linking PEG-Fc to the N-terminus or the $29^{th}$ lysine residue of the insulin beta chain, respectively and binding affinities of the respective insulin conjugates to insulin receptors were examined. As a result, the insulin conjugate prepared by linking PEG-Fc to the $29^{th}$ lysine residue of the insulin beta chain showed higher binding affinity (about 3.6 times) than the insulin conjugate prepared by linking PEG-Fc to the N-terminus of the insulin beta chain (Example 4, Table 1). Such an increase in insulin receptor binding affinity indicates increased activity of the corresponding insulin conjugate.

However, the binding site of the non-peptidyl polymer for the preparation of a conjugate that maintains insulin activity and has improved stability is not limited to the $29^{th}$ residue of the insulin beta chain. The conjugates prepared by linking the non-peptidyl polymer to the insulin beta chain, preferably C-terminal region, more preferably any one of the amino acid residues at positions 20 to 29, and much more preferably any one of the amino acid residues at positions 25 to 29 are also included in the scope of the present invention. For example, native insulin may be covalently linked to the non-peptidyl polymer via the ε-amine group of the sole lysine residue at position 29 of the beta chain. An insulin variant or derivative containing an amino acid residue having an amine group or a thiol group at other sites may be also linked with the non-peptidyl polymer at the corresponding amino acid position, and these conjugates are also included in the scope of the present invention.

When the conjugate maintaining insulin activity is prepared, the amino acid residue of the insulin beta chain may be replaced with a lysine or cysteine residue for convenient preparation. For example, an insulin derivative formed by replacing the amino acid residue at the C-terminus of the insulin beta chain with a lysine or cysteine residue is used to prepare an insulin conjugate with ease, and an insulin conjugate prepared by using this insulin derivative is also included in the scope of the present invention.

As used herein, "non-peptidyl polymer" means a biocompatible polymer formed by linking two or more of repeating units, and the repeating units are linked to each other via not a peptide bond but any covalent bond. The non-peptidyl polymer useful in the present invention may be selected from the group consisting of polyethylene glycol, polypropylene glycol, an ethylene glycol-propylene glycol copolymer, polyoxyethylated polyol, polyvinyl alcohol, polysaccharide, dextran, polyvinyl ethyl ether, a biodegradable polymer such as PLA (polylactic acid) and PLGA (polylactic-glycolic acid), a lipid polymer, chitin, hyaluronic acid, and combinations thereof, and preferably, polyethylene glycol (PEG). The derivatives thereof which are well known in the art and easily prepared within the skill of the art are also included in the scope of the present invention.

The peptide linker which is used in the fusion protein obtained by a conventional in frame fusion method has drawbacks in that it is easily cleaved in vivo by a proteolytic enzyme, and thus a sufficient effect of increasing the blood half-life of the active drug by a carrier cannot be obtained as expected. In the present invention, however, the polymer having resistance to the proteolytic enzyme may be used to maintain the blood half-life of the peptide similar to that of the carrier. Therefore, any non-peptidyl polymer may be used without limitation, as long as it is a polymer having the aforementioned function, that is, a polymer having resistance to the in vivo proteolytic enzyme. The non-peptidyl polymer has a molecular weight ranging from 1 to 100 kDa, and preferably, ranging from 1 to 20 kDa. Further, the non-peptidyl polymer of the present invention, linked to the physiologically active polypeptide, may be one polymer or a combination of different types of polymers.

The non-peptidyl polymer used in the present invention has a reactive group capable of binding to the immunoglobulin Fc region and the protein drug.

Preferably, the non-peptidyl polymer may bind to the amine group or thiol group of the side chain of the amino acid residue of the insulin beta chain to form a peptide, hemithioacetal, imine or thiodioxopyrrolidinyl bond.

Non-limiting examples of the reactive groups at both ends of the non-peptidyl polymer may include an aldehyde group such as a propionaldehyde group or a butyraldehyde group, a maleimide group, and a succinimide derivative. The succinimide derivative may be succinimidyl carboxymethyl, succinimidyl valerate, succinimidyl methyl butanoate, succinimidyl methyl propionate, succinimidyl butanoate, succinimidyl propionate, N-hydroxysuccinimide or succinimidyl carbonate, but is not limited thereto. Any reactive group that is selectively able to form a covalent bond, together with the amine or thiol group of the amino acid residue of the immunoglobulin Fc region and the insulin beta chain may be used without limitation.

The reactive groups at both ends of the non-peptidyl polymer may be the same as or different from each other. For example, the non-peptide polymer may possess a succinimide group at one end, and an aldehyde group such as a propionaldehyde group or a butyraldehyde group at the other end. When polyethylene glycol having reactive hydroxy groups at both ends thereof is used as the non-peptidyl polymer, the hydroxy group may be activated to various reactive groups by known chemical reactions, or polyethylene glycol having a commercially available modified reactive group may be used so as to prepare the protein conjugate of the present invention.

Preferably, the non-peptidyl polymer may have a butyraldehyde group and a succinimidyl valerate reactive group at both ends, respectively.

As used herein, "immunoglobulin Fc region" refers to a protein that contains the heavy-chain constant region 2 (CH2) and the heavy-chain constant region 3 (CH3) of an immunoglobulin, excluding the variable regions of the heavy and light chains, the heavy-chain constant region 1 (CH1) and the light-chain constant region 1 (CL1) of the immunoglobulin. It may further include a hinge region at the heavy-chain constant region. Also, the immunoglobulin Fc region of the present invention may contain a part or all of the Fc region including the heavy-chain constant region 1 (CH1) and/or the light-chain constant region 1 (CL1), except for the variable regions of the heavy and light chains of the immunoglobulin, as long as it has an effect substantially similar to or better than that of the native form. Also, it may be a region having a deletion in a relatively long portion of the amino acid sequence of CH2 and/or CH3. That is, the immunoglobulin Fc region of the present invention may include 1) a CH1 domain, a CH2 domain, a CH3 domain and a CH4 domain, 2) a CH1 domain and a CH2 domain, 3) a CH1 domain and a CH3 domain, 4) a CH2 domain and a CH3 domain, 5) a combination of one or more domains and an immunoglobulin hinge region (or a portion of the hinge region), and 6) a dimer of each domain of the heavy-chain constant regions and the light-chain constant region.

The immunoglobulin Fc region is safe for use as a drug carrier because it is a biodegradable polypeptide that is metabolized in vivo. Also, the immunoglobulin Fc region has a relatively low molecular weight, as compared to the whole immunoglobulin molecules, and thus, it is advantageous in terms of preparation, purification and yield of the conjugate. The immunoglobulin Fc region does not contain a Fab fragment, which is highly non-homogenous due to different amino acid sequences according to the antibody subclasses, and thus it can be expected that the immunoglobulin Fc region may greatly increase the homogeneity of substances and be less antigenic in blood.

The immunoglobulin Fc region may be derived from humans or other animals including cows, goats, swine, mice, rabbits, hamsters, rats and guinea pigs, and preferably, humans. In addition, the immunoglobulin Fc region may be an Fc region that is derived from IgG, IgA, IgD, IgE, and IgM, or made by combinations thereof or hybrids thereof. Preferably, it is derived from IgG or IgM, which are among the most abundant proteins in human blood, and most preferably, from IgG which is known to enhance the half-lives of ligand-binding proteins.

Meanwhile, "combination", as used herein, means that polypeptides encoding single-chain immunoglobulin Fc regions of the same origin are linked to a single-chain polypeptide of a different origin to form a dimer or multimer. That is, a dimer or multimer may be formed from two or more fragments selected from the group consisting of IgG Fc, IgA Fc, IgM Fc, IgD Fc and IgE Fc fragments.

As used herein, "hybrid" means that sequences encoding two or more immunoglobulin Fc regions of different origin are present in a single-chain immunoglobulin Fc region. In the present invention, various types of hybrids are possible. That is, domain hybrids composed of one to four domains selected from the group consisting of CH1, CH2, CH3 and CH4 of IgG Fc, IgM Fc, IgA Fc, IgE Fc and IgD Fc are possible, and may include the hinge region.

On the other hand, IgG is divided into IgG1, IgG2, IgG3 and IgG4 subclasses, and the present invention includes combinations and hybrids thereof. Preferred are IgG2 and IgG4 subclasses, and most preferred is the Fc region of IgG4 rarely having effector functions such as CDC (complement dependent cytotoxicity).

That is, as the drug carrier of the present invention, the most preferable immunoglobulin Fc region is a human IgG4-derived non-glycosylated Fc region. The human-derived Fc region is more preferable than a non-human derived Fc region which may act as an antigen in the human body and cause undesirable immune responses such as the production of a new antibody against the antigen.

Meanwhile, the immunoglobulin Fc region may be in the form of having native sugar chains, increased sugar chains compared to a native form or decreased sugar chains compared to the native form, or may be in a deglycosylated form. The increase, decrease or removal of the immunoglobulin Fc sugar chains may be achieved by methods common in the art, such as a chemical method, an enzymatic method and a genetic engineering method using a microorganism. Here, the removal of sugar chains from an Fc region results in a sharp decrease in binding affinity to the complement (c1q) and a decrease or loss in antibody-dependent cell-mediated cytotoxicity or complement-dependent cytotoxicity, thereby not inducing unnecessary immune responses in vivo. In this regard, an immunoglobulin Fc region in a deglycosylated or aglycosylated form may be more suitable to the object of the present invention as a drug carrier.

As used herein, "deglycosylation" means to enzymatically remove sugar moieties from an Fc region, and "aglycosylation" means that an Fc region is produced in an unglycosylated form by a prokaryote, preferably, E. coli.

Further, the immunoglobulin Fc region of the present invention includes a sequence derivative (mutant) thereof as well as a native amino acid sequence. An amino acid sequence derivative has a sequence that is different from the native amino acid sequence due to deletion, insertion, non-conservative or conservative substitution of one or more amino acid residues, or combinations thereof. For example, in IgG Fc, amino acid residues known to be important in binding, at positions 214 to 238, 297 to 299, 318 to 322, or 327 to 331, may be used as a suitable target for modification. In addition, other various derivatives are possible, including derivatives having a deletion of a region capable of forming a disulfide bond, a deletion of several amino acid residues at the N-terminus of a native Fc form, or an addition of a methionine residue to the N-terminus of a native Fc form. Furthermore, to remove effector functions, a deletion may occur in a complement-binding site, such as a C1q-binding site and an ADCC (antibody dependent cell mediated cytotoxicity) site. Techniques of preparing such sequence derivatives of the immunoglobulin Fc region are disclosed in WO 97/34631 and WO 96/32478.

Amino acid exchanges in proteins and peptides, which do not generally alter the activity of molecules, are known in the art (H. Neurath, R. L. Hill, The Proteins, Academic Press, New York, 197 9). The most commonly occurring exchanges are Ala/Ser, Val/Ile, Asp/Glu, Thr/Ser, Ala/Gly, Ala/Thr, Ser/Asn, Ala/Val, Ser/Gly, Thr/Phe, Ala/Pro, Lys/Arg, Asp/Asn, Leu/Ile, Leu/Val, Ala/Glu, Asp/Gly, in both directions.

The Fc region, if desired, may be modified by phosphorylation, sulfation, acrylation, glycosylation, methylation, farnesylation, acetylation, amidation or the like.

The aforementioned Fc derivatives are derivatives that have a biological activity identical to that of the immunoglobulin Fc region of the present invention or improved structural stability against heat, pH, or the like. In addition, these immunoglobulin constant regions may be obtained from native forms isolated from humans and other animals including cows, goats, swine, mice, rabbits, hamsters, rats and guinea pigs, or may be recombinants or derivatives thereof, obtained from transformed animal cells or microorganisms. Here, they may be obtained from a native immunoglobulin by isolating whole immunoglobulins from human or animal organisms and treating them with a proteolytic enzyme. Papain digests the native immunoglobulin into Fab and Fc regions, and pepsin treatment results in the production of pF'c and F(ab)$_2$. These fragments may be subjected to size-exclusion chromatography to isolate Fc or pF'c.

Preferably, a human-derived immunoglobulin Fc region may be a recombinant immunoglobulin constant region that is obtained from a microorganism.

In the present invention, binding of the immunoglobulin Fc region and the non-peptidyl polymer is formed by a covalent bond between the other terminal reactive group of the non-peptidyl polymer that does not bind with insulin and the amine or thiol group of the amino acid residue of the immunoglobulin Fc region, like as binding of the insulin beta chain and the non-peptidyl polymer. Therefore, the non-peptidyl polymer binds to the N-terminus of the immunoglobulin Fc region, or the amine group of the lysine residue or the thiol group of the cysteine residue within the immunoglobulin Fc region. In this regard, there is no limitation in the position of the amino acid residue on the immunoglobulin Fc region, to which the non-peptidyl polymer binds.

In still another aspect, the present invention provides a long-acting insulin formulation with improved in vivo activity, including the insulin conjugate. The long-acting formulation may be a composition for the treatment of diabetes.

Further, the present invention provides a method for treating diabetes by administering the long-acting insulin formulation to a subject in need thereof.

As used herein, "administration" means introduction of a predetermined substance into a patient by a certain suitable method. The conjugate of the present invention may be administered via any of the common routes, as long as it is able to reach a desired tissue. Intraperitoneal, intravenous, intramuscular, subcutaneous, intradermal, oral, topical, intranasal, intrapulmonary and intrarectal administration can be performed, but the present invention is not limited thereto. However, since peptides are digested upon oral administration, active ingredients of a composition for oral administration should be coated or formulated for protection against degradation in the stomach. Preferably, the present composition may be administered in an injectable form. In addition, the long-acting formulation may be administered using a certain apparatus capable of transporting the active ingredients into a target cell.

The long-acting formulation including the conjugate of the present invention may include pharmaceutically acceptable carriers. For oral administration, the pharmaceutically acceptable carrier may include a binder, a lubricant, a disintegrator, an excipient, a solubilizer, a dispersing agent, a stabilizer, a suspending agent, a coloring agent, a perfume or the like. For injectable preparations, the pharmaceutically acceptable carrier may include a buffering agent, a preserving agent, an analgesic, a solubilizer, an isotonic agent, and a stabilizer. For preparations for topical administration, the pharmaceutically acceptable carrier may include a base, an excipient, a lubricant, a preserving agent or the like. The long-acting formulation of the present invention may be formulated into a variety of dosage forms in combination with the aforementioned pharmaceutically acceptable carriers. For example, for oral administration, the formulation may be prepared into tablets, troches, capsules, elixirs, suspensions, syrups or wafers. For injectable preparations, the formulation may be prepared into a single-dose ampule or multidose container. The formulation may be also formulated into solutions, suspensions, tablets, pills, capsules and sustained release preparations.

On the other hand, examples of carriers, excipients and diluents suitable for formulation include lactose, dextrose, sucrose, sorbitol, mannitol, xylitol, erythritol, maltitol, starch, acacia, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate, mineral oils or the like. In addition, the formulation may further include fillers, anti-coagulating agents, lubricants, humectants, perfumes, antiseptics or the like.

Further, the long-acting formulation of the present invention may be determined by several related factors including the types of diseases to be treated, administration routes, the patient's age, gender, weight and severity of the illness, as well as by the types of the drug as an active component. Since the pharmaceutical composition of the present invention has excellent in vivo duration and titer, it greatly reduces administration frequency of the pharmaceutical formulation of the present invention.

The long-acting formulation of the present invention improves in vivo stability of insulin while maintaining its activity, and thus it is effective for the treatment of diabetes.

In still another aspect, the present invention provides a preparation method of the insulin conjugate, including the steps of: (1) covalently linking a non-peptidyl polymer to an amino acid residue of the insulin beta chain excluding the N-terminus thereof; (2) isolating an insulin complex, in which the non-peptidyl polymer is covalently linked to the amino acid residue of the insulin beta chain excluding the N-terminus thereof, from the reaction mixture of (1); and (3) covalently linking an immunoglobulin Fc region to the other end of the non-peptidyl polymer of the isolated linkage so as to produce an insulin conjugate, in which the immunoglobulin Fc region and insulin are linked to each end of the non-peptidyl polymer.

As described above, the non-peptidyl polymer may preferably bind to the amine group or thiol group of the side chain of the amino acid residue of the insulin beta chain to form a peptide, hemithioacetal, imine or thiodioxopyrrolidinyl bond. In this regard, both ends of the non-peptidyl polymer are each independently an aldehyde derivative, a maleimide derivative, or a succinimide derivative as a reactive group, but are not limited thereto.

As described above, both ends of the non-peptidyl polymer may preferably bind to the amine group or thiol group of the side chain of the amino acid residue of the insulin beta chain excluding the N-terminus thereof and the immunoglobulin Fc region, respectively.

Preferably, the non-peptidyl polymer may have an aldehyde derivative and a succinimide derivative as a reactive group at both ends, respectively. In this regard, Step (1) may be performed under an alkaline environment of pH 9.0±2. If the reaction may be allowed under an acidic environment of lower than pH 7, the non-peptidyl polymer may bind to the N-terminal amine group. The above pH range may be controlled, depending on the kind of the reactive group of the non-peptidyl polymer and the kind of the reactive group of the amino acid residue of the insulin beta chain, which reacts therewith, for example, an amine group or thiol group. For example, if PEG having a succinimide derivative as a reactive group is used as the non-peptidyl polymer and is intended to be linked to the amine group of lysine within insulin, pH is controlled to 9.0, leading to formation of an insulin complex, in which the non-peptidyl polymer selectively binds to the amine group of lysine, not to the N-terminal amine group.

In Step (1) of linking the non-peptidyl polymer to the insulin beta chain, a reaction molar ratio of insulin and the polymer may be preferably 1:1.5 to 1:10, and more preferably 1:2. Further, in Step (3) of covalently linking the immunoglobulin Fc region to the other end of the non-peptidyl polymer of the insulin complex, a molar ratio of the insulin complex and the immunoglobulin Fc region may be preferably 1:1 to 1:10, and more preferably 1:1.2.

Figure 2:
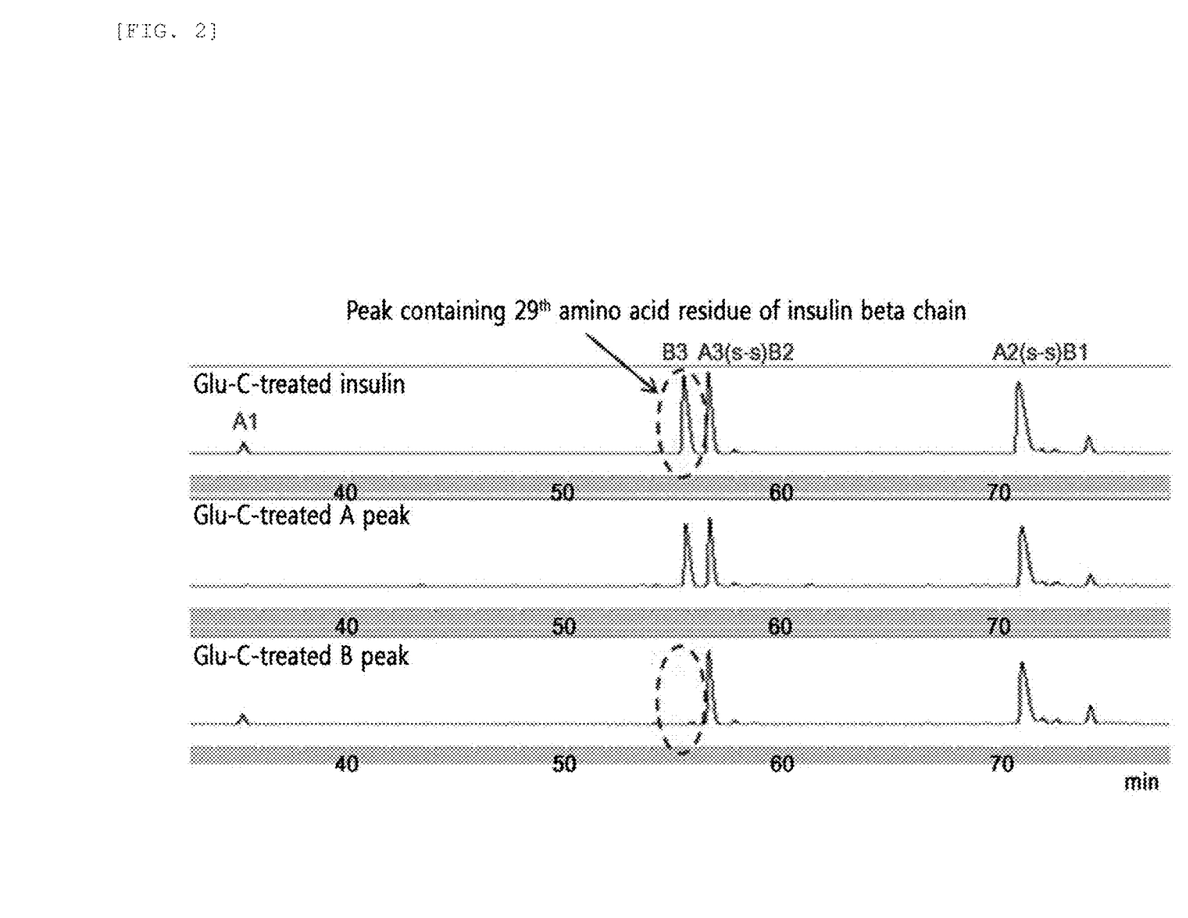
Figure 3:
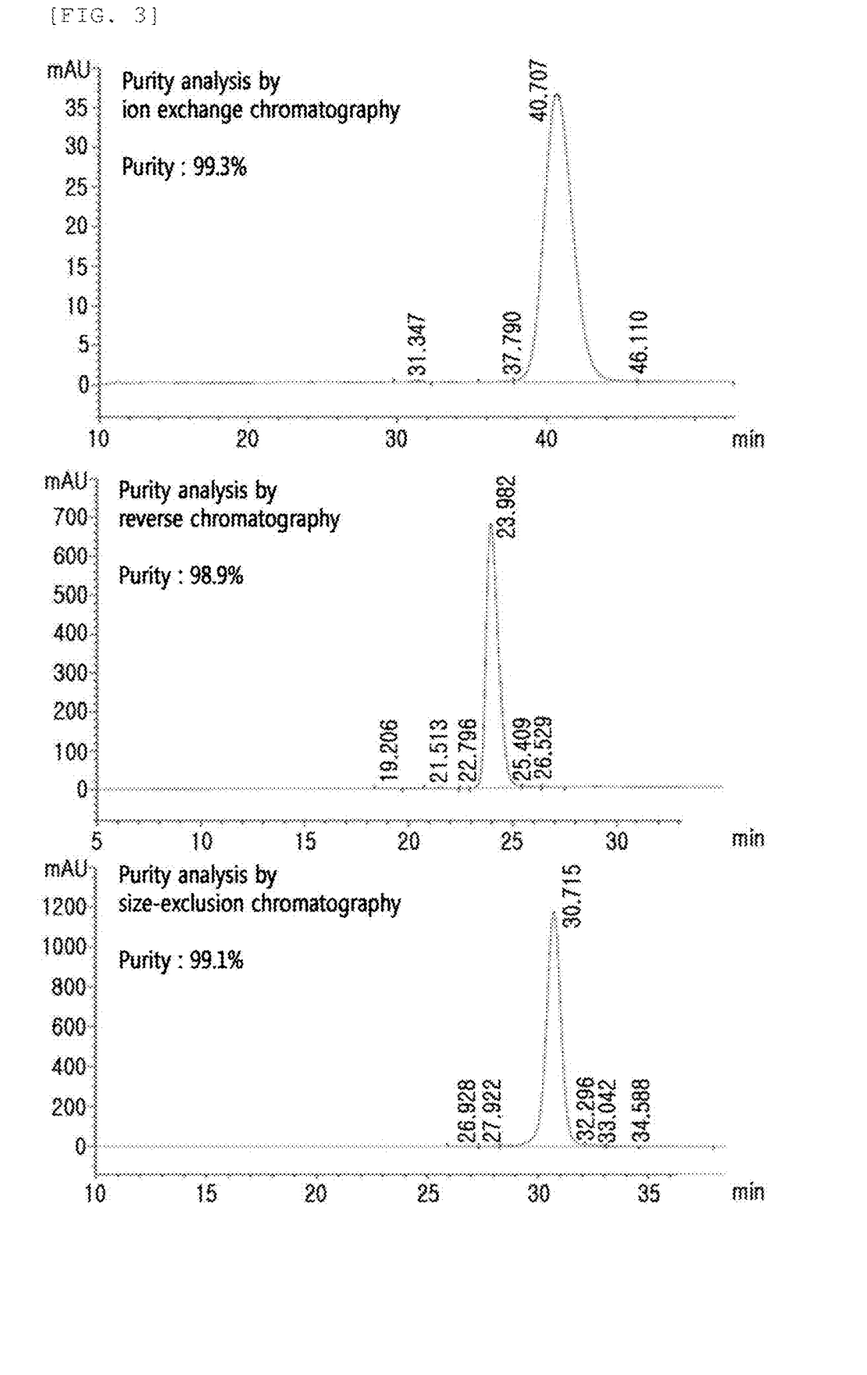
FIG. 3 shows the result of analyzing purity of the final purified conjugate.

In a specific embodiment of the present invention, insulin is selectively pegylated in a high yield using a PEG linker that independently contains each of succinimide and aldehyde reactive groups at both ends, and the pegylation of the $29^{th}$ residue of the insulin beta chain was identified by a mapping method (FIGS. 2 to 3). Further, the present inventors linked an immunoglobulin constant region to the mono-pegylated insulin thus prepared so as to prepare an insulin-non-peptidyl polymer-immunoglobulin constant region conjugate.

Binding affinity of the prepared insulin conjugate to the insulin receptor was examined. As a result, the insulin conjugate showed about 3.6 times higher binding affinity than the conjugate prepared by linking PEG-Fc to the N-terminus of insulin, indicating superior efficacy of the conjugate of the present invention.

Hereinafter, the present invention will be described in more detail with reference to Examples. However, these Examples are for illustrative purposes only, and the invention is not intended to be limited by these Examples.

Figure 1A:
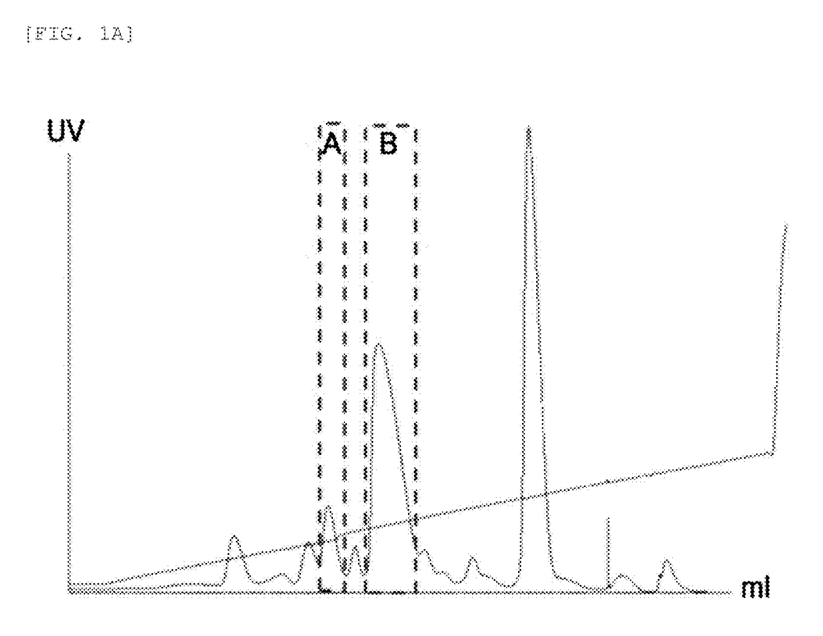
Figure 1B:
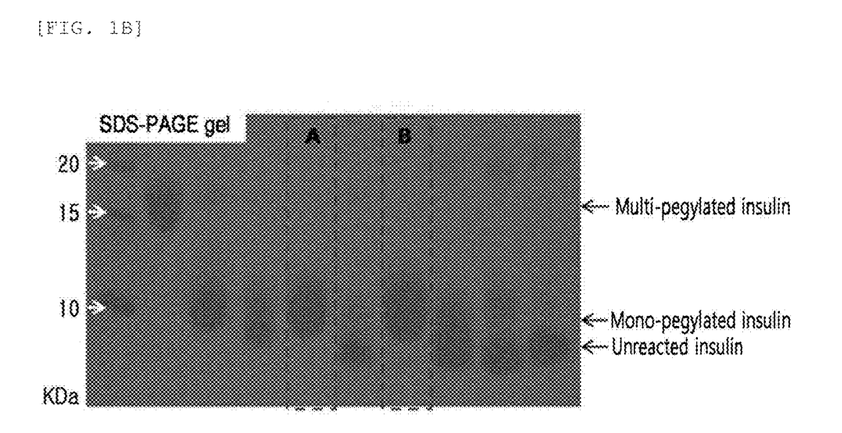

Example 1: PEGylation Reaction of $29^{th}$ Amino Acid of Beta Chain of Insulin and Purification of Mono-Pegylated Insulin Insulin powder was dissolved in 10 mM HCl, and then reacted with 3.4K butyraldehyde-PEG-succinimidyl valerate (PEG having a butyl aldehyde group and a succinimidyl valerate group as functional groups at each end, Laysan Bio, Inc., USA) at room temperature for about 1 hour at a molar ratio of insulin:PEG of 1:2 and an insulin concentration of 1.5 mg/mL to pegylate the $29^{th}$ amino acid residue of the insulin beta chain. This reaction was conducted in 60.8 mM sodium borate and 45% isopropanol at pH 9.0. The reaction solution was purified with Source S (GE Healthcare) column using a buffer containing sodium citrate (pH 3.0) and 45% ethanol, and a KCl concentration gradient to give mono-pegylated insulin (FIGS. 1a to 1b).

Example 2: Identification of Pegylation Site of Mono-Pegylated Insulin

In order to identify the 3.4K PEG binding site in the insulin pegylated according to Example 1, a Glu-C mapping method was used. 10 µg of endoproteinase Glu-C with a concentration of 1 mg/mL was added to 50 µg of mono-pegylated insulin with a concentration of 1 mg/mL. The reaction solution was 50 mM HEPES at pH 7.5, and the reaction was allowed at 25° C. for 8 hours. Then, 50 µL of 1 N HCl was added to terminate the reaction. HPLC reverse chromatography was used for mapping. The result is given in FIG. 2.

As shown in FIG. 2, a shift of the peak containing the $29^{th}$ amino acid of the insulin beta chain was observed, indicating pegylation of the $29^{th}$ amino acid of the insulin beta chain with 3.4K PEG.

Example 3: Preparation of Conjugate of Mono-Pegylated Insulin and Immunoglobulin Fc To prepare an insulin-PEG-immunoglobulin Fc fragment conjugate, mono-PEGylated insulin prepared by the method of Example 1 and an immunoglobulin Fc fragment were reacted at a molar ratio of 1:1.2 with a total protein level of 20 mg/mL at 25° C. for 13 hours. In this regard, the reaction solution contained 100 mM HEPES and 2 M sodium chloride (NaCl) at pH 8.2, and further contained 20 mM sodium cyanoborohydride as a reducing agent.

After completion of the reaction, the reaction solution was passed through Source Q (GE Healthcare) column to separate and purify the unreacted insulin, the unreacted immunoglobulin Fc fragment, the insulin-PEG-immunoglobulin Fc fragment conjugate, and the conjugate of immunoglobulin Fc fragment coupled with two or more mono-PEGylated insulin (insulin-PEG) using Tris-HCl (pH 7.5) buffer and a NaCl concentration gradient.

Then, Source ISO (GE Healthcare) was used to remove any residual immunoglobulin Fc and multi-coupled insulin conjugate, thereby obtaining the insulin-PEG-immunoglobulin Fc conjugate. In this case, the elution was conducted using a concentration gradient of ammonium sulfate containing Tris-HCl (pH 7.5). The purity of the conjugate thus prepared was analyzed by HPLC using reverse chromatography, ion exchange chromatography, and size exclusion chromatography (FIG. 3).

Example 4: Measurement of Insulin Receptor Binding Affinity of Insulin Conjugate According to PEG-Fc Binding Site within Insulin Beta Chain In order to measure insulin receptor binding affinities of an insulin conjugate prepared by linking PEG-Fc to the N-terminus of insulin and an insulin conjugate by linking PEG-Fc to B29, SPR (surface Plasmon resonance, BIA-CORE 3000) was used. As the insulin receptors, ECD (extracellular domain) was expressed in HEK293F cell, and then purified. The insulin receptors thus expressed were immobilized on a CM5 chip by amine coupling, and 1 μM to 6.25 nM of the N-terminus or B29 insulin conjugate were applied and their binding affinities were measured. These insulin conjugates were diluted using a binding buffer (HBS-EP), and bound to the insulin conjugate-immobilized chip for 4 minutes, and dissociated for 6 minutes. Then, to bind the insulin conjugates at different concentrations, 50 mM NaCl/5 mM NaH was applied to the insulin conjugates coupled with the insulin receptors for about 30 seconds. The binding affinity was analyzed using 1:1 Langmuir binding model of BIAevaluation software program. The results are given in FIG. 4.

Figure 4:
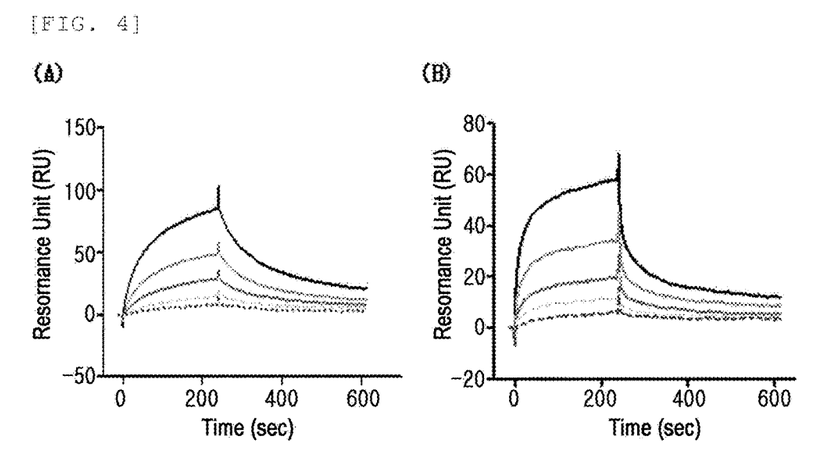
FIG. 4 shows sensorgrams of binding of the insulin conjugate to insulin receptor, in which (A) represents a N-terminus insulin conjugate, (B) represents a B29 insulin conjugate, and each curve from top to bottom represents the substance concentration of 1000, 500, 250, 125, or 62.5 nM.

As shown in FIG. 4, both the N-terminus and B29 insulin conjugates were found to bind with insulin receptors in a concentration-dependent manner. Binding affinities of these insulin conjugates to insulin receptors are shown in Table 1. In detail, the B29 insulin conjugate has an association rate constant which is about 1.8 times higher than that of the N-terminus insulin conjugate, indicating that binding of the B29 insulin conjugate to the insulin receptor is faster than that of the N-terminus insulin conjugate. The B29 insulin conjugate has a dissociation rate constant which is about 1.8 times lower than that of the N-terminus insulin conjugate, indicating that after binding, binding of the B29 insulin conjugate to the insulin receptor is maintained more stably. The results of comparing the binding affinity between the N-terminus and B29 insulin conjugates showed that the binding affinity of the B29 insulin conjugate is about 3.6 times higher than that of the N-terminus insulin conjugate.

TABLE 1

Comparison of insulin receptor binding affinity between N-terminus insulin conjugate and B29 insulin conjugate

| Insulin conjugate | $k_a$ (1/ms, ×10$^5$) | $k_d$ (1/s, ×10$^3$) | $K_D$ (nM) |
|---|---|---|---|
| N-terminus | 0.06 ± 0.01 | 3.86 ± 0.15 | 692.5 ± 50.2 |
| B29 | 0.11 ± 0.02 | 2.15 ± 0.22 | 191.5 ± 50.2 |

$k_a$: association rate constant
$k_d$: dissociation rate constant
$K_D$: affinity constant Based on the above description, it will be apparent to those skilled in the art that various modifications and changes may be made without departing from the scope and spirit of the invention. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

EFFECT OF THE INVENTION

The insulin conjugate of the present invention exhibits a remarkably increased binding affinity to insulin receptors, and thus in vivo activity of insulin is greatly improved, thereby being used in the development of a long-acting insulin formulation with high efficiency.

What is claimed is:

1. An insulin conjugate, wherein insulin and an immunoglobulin Fc region are covalently linked to each other via a non-peptidyl polymer selected from the group consisting of polyethylene glycol, polypropylene glycol, an ethylene glycol-propylene glycol copolymer, polyoxyethylated polyol, polyvinyl alcohol, polyvinyl ethyl ether, PLA (polylactic acid), PLGA (polylactic-glycolic acid), and a combination thereof, and one end of the non-peptidyl polymer is linked to any one of amino acid residues at positions 25 to 29 of an insulin beta chain and the other end thereof is linked to the immunoglobulin Fc region, wherein reactive groups on both ends of the non-peptidyl polymer each independently are linked to amine group or thiol group of the amino acid residue of the insulin beta chain and amine group or thiol group of amino acid residue of the immunoglobulin Fc region to form a covalent bond, the amine group is present in the N-terminus or side chain of lysine residue of the immunoglobulin Fc region and the N-terminus or side chain of lysine residue of the insulin beta chain, and the thiol group is present in side chain of cysteine residue of the immunoglobulin Fc region and side chain of cysteine residue of the insulin beta chain; and wherein the insulin is selected from the group consisting of the following (i)-(iv):

(i) a native insulin comprising a first peptide of SEQ ID NO: 1 and a second peptide of SEQ ID NO: 2;

(ii) an insulin variant which comprises a first peptide of SEQ ID NO: 1 and a second peptide of SEQ ID NO: 2, in which one amino acid residue of SEQ ID NO: 1 and/or one amino acid residue of SEQ ID NO: 2 is different from the amino acid sequence of the native insulin (i) by way of substitution, deletion, modification, and/or addition, wherein the insulin variant retains a function of controlling blood glucose level in a body of subject to which said insulin variant is administered;

(iii) an insulin derivative peptide, wherein a chemical group of one amino acid residue of SEQ ID NO: 1 and/or one amino acid residue of SEQ ID NO: 2 is chemically modified, and wherein the insulin derivative peptide retains a function of controlling blood glucose level in a body of subject to which said insulin derivative peptide is administered; and (iv) a fragment of the native insulin (i), said fragment having one amino acid deleted at the N-terminus and/or one amino acid deleted at the C-terminus of the native insulin (i), or having a nonnaturally occurring amino acid, wherein the fragment retains a function of controlling blood glucose level in a body of subject to which said fragment is administered.

2. The insulin conjugate of claim 1, wherein the non-peptidyl polymer is linked to any one of the amino acid residues at positions 25 to 28 of the insulin beta chain.

3. The insulin conjugate of claim 1, wherein the non-peptidyl polymer is linked to the lysine residue at position 29 of the insulin beta chain.

4. The insulin conjugate of claim 1, wherein the amino acid, to which the non-peptidyl polymer is linked, is a naturally occurring or non-naturally occurring amino acid.

5. The insulin conjugate of claim 1, wherein the immunoglobulin Fc region is aglycosylated.

6. The insulin conjugate of claim 1, wherein the immunoglobulin Fc region is composed of one to four domains selected from the group consisting of CH1, CH2, CH3 and CH4 domains.

7. The insulin conjugate of claim 6, wherein the immunoglobulin Fc region further includes a hinge region.

8. The insulin conjugate of claim 1, wherein the immunoglobulin Fc region is an Fc region derived from IgG, IgA, IgD, IgE or IgM.

9. The insulin conjugate of claim 8, wherein each domain of the immunoglobulin Fc region is a hybrid of domains of a different origin derived from an immunoglobulin selected from the group consisting of IgG, IgA, IgD, IgE, and IgM.

10. The insulin conjugate of claim 8, wherein the immunoglobulin Fc region is a dimer or a multimer composed of single-chain immunoglobulins composed of domains of the same origin.

11. The insulin conjugate of claim 8, wherein the immunoglobulin Fc region is an IgG4 Fc region.

12. The insulin conjugate of claim 8, wherein the immunoglobulin Fc region is a human aglycosylated IgG4 Fc region.

13. The insulin conjugate of claim 1, wherein the non-peptidyl polymer binds to the amine group or thiol group of the side chain of the amino acid residue of the insulin beta chain to form a peptide, hemithioacetal, imine or thiodioxopyrrolidinyl bond.

14. The insulin conjugate of claim 1, wherein both ends of the non-peptidyl polymer each independently have a reactive group selected from the group consisting of an aldehyde group, a propionaldehyde group, a butyraldehyde group, a maleimide group, and a succinimide derivative.

15. The insulin conjugate of claim 14, wherein the succinimide derivative is succinimidyl carboxymethyl, succinimidyl valerate, succinimidyl methyl butanoate, succinimidyl methyl propionate, succinimidyl butanoate, succinimidyl propionate, N-hydroxysuccinimide, or succinimidyl carbonate.

16. The insulin conjugate of claim 14, wherein both ends of the non-peptidyl polymer have a butyraldehyde reactive group and a succinimidyl valerate reactive group, respectively.

17. A long-acting insulin formulation having improved in vivo duration and stability, comprising the insulin conjugate of claim 1.

18. The long-acting insulin formulation of claim 17, wherein the formulation is used for the treatment of diabetes.

19. A preparation method of the insulin conjugate of claim 1, comprising the steps of:

(1) covalently linking a non-peptidyl polymer to an amino acid residue of the insulin beta chain excluding the N-terminus thereof;

(2) isolating an insulin complex, in which the non-peptidyl polymer is covalently linked to the amino acid residue of the insulin beta chain excluding the N-terminus thereof, from the reaction mixture of (1); and (3) covalently linking an immunoglobulin Fc region to the other end of the non-peptidyl polymer of the isolated complex so as to produce an insulin conjugate, in which the immunoglobulin Fc region and insulin are linked to each end of the non-peptidyl polymer.

20. The method of claim 19, wherein the non-peptidyl polymer binds to the amine group or thiol group of the side chain of the amino acid residue of the insulin beta chain to form a peptide, hemithioacetal, imine or thiodioxopyrrolidinyl bond.

21. The method of claim 19, wherein both ends of the non-peptidyl polymer each independently have an aldehyde derivative, a maleimide derivative, or a succinimide derivative as a reactive group.

22. The method of claim 19, wherein both ends of the non-peptidyl polymer are linked to an amine group or a thiol group of the side chain of the amino acid residue of the insulin beta chain excluding the N-terminus thereof and an immunoglobulin Fc region, respectively.

23. The method of claim 19, wherein both ends of the non-peptidyl polymer each independently have a butyraldehyde group or a succinimidyl valerate reactive group.

24. The method of claim 19, wherein Step (1) is performed under an alkaline environment of pH 9.0±2.

25. The method of claim 19, wherein a molar ratio of the insulin and the non-peptidyl polymer in Step (1) is 1:1.5 to 1:10.

26. The method of claim 19, wherein a molar ratio of the insulin complex and the immunoglobulin Fc region in Step (3) is 1:1 to 1:10.

27. The insulin conjugate of claim 1, wherein the non-peptidyl polymer is polyethylene glycol, and, in the conjugate, the non-peptidyl polymer is linked to N-terminus of the immunoglobulin Fc region.

28. The insulin conjugate of claim 1, wherein the non-peptidyl polymer has a molecular weight in a range from 1 kDa to 100 kDa.

29. The insulin conjugate of claim 1, wherein the non-peptidyl polymer has a molecular weight in a range from 1 kDa to 20 kDa.

30. The insulin conjugate of claim 1, wherein the insulin is the native insulin, or the insulin variant which comprises a first peptide of SEQ ID NO: 1 and a second peptide of SEQ ID NO: 2, in which one amino acid residue of SEQ ID NO: 1 and/or one amino acid residue of SEQ ID NO: 2 is different from the amino acid sequence of the native insulin by way of substitution, wherein the insulin variant retains a function of controlling blood glucose level in a body of subject to which said insulin variant is administered.

* * * * *